(12) United States Patent
Vandenbooren et al.

(10) Patent No.: US 7,291,754 B2
(45) Date of Patent: Nov. 6, 2007

(54) PROCESS FOR THE CATALYTIC HYDROGENATION OF A NITRILE

(75) Inventors: Franciscus H. A. M. Vandenbooren, Maastricht (NL); Hubertus J. M. Bosman, Sittard (NL); Alexander V. Peters, Aachen (DE); Maria J. G. Van Den Boer, Houthalen-Helchteren (BE)

(73) Assignee: DSM IP Assets B.V., Te Heerlen (NL)

( * ) Notice: Subject to any disclaimer, the term of this patent is extended or adjusted under 35 U.S.C. 154(b) by 237 days.

(21) Appl. No.: 10/541,585

(22) PCT Filed: Jan. 21, 2004

(86) PCT No.: PCT/NL2004/000050

§ 371 (c)(1),
(2), (4) Date: Jul. 7, 2005

(87) PCT Pub. No.: WO2004/066703

PCT Pub. Date: Aug. 12, 2004

(65) Prior Publication Data

US 2006/0122433 A1    Jun. 8, 2006

(30) Foreign Application Priority Data

Jan. 31, 2003  (EP) .................................. 03075306

(51) Int. Cl.
*C07C 209/48*   (2006.01)

(52) U.S. Cl. ..................... 564/492; 564/415; 564/490; 564/491; 564/493

(58) Field of Classification Search .................... None
See application file for complete search history.

(56) References Cited

U.S. PATENT DOCUMENTS

| 3,896,051 A | 7/1975 | Mabuchi et al. |
| 5,574,181 A | 11/1996 | Bosman et al. |
| 5,777,166 A | 7/1998 | Cordier et al. |

FOREIGN PATENT DOCUMENTS

| GB | 833592 | 4/1960 |
| WO | WO 99/335561 | 7/1999 |
| WO | WO 01/66511 | 9/2001 |

OTHER PUBLICATIONS

International Search Report, 2004.

*Primary Examiner*—Brian Davis
(74) *Attorney, Agent, or Firm*—Nixon & Vanderhye PC

(57) ABSTRACT

Process for the catalytic hydrogenation of a nitrite in the presence of an amine and a catalyst wherein the catalyst is a liquid-rinsed Raney-type catalyst contacted with a hydroxide prior to contacting the catalyst with the amine. The process results in higher selectivity in the formation of diamines from diniriles.

11 Claims, No Drawings

PROCESS FOR THE CATALYTIC HYDROGENATION OF A NITRILE

This application is the US national phase of international application PCT/NL2004/000050 filed 21 Jan. 2004 which designated the U.S. and claims benefit of EP 03075306.5, dated 31 Jan. 2003, the entire content of which is hereby incorporated by reference.

The invention relates to a process for the catalytic hydrogenation of a nitrile in the presence of an amine, a hydroxide and a freshly prepared and liquid-rinsed Raney-type catalyst.

Such a process is known from U.S. Pat. No. 5,777,166. In the known process, the catalyst, being a Raney nickel type catalyst with at least one additional metal element selected from Group IVb of the Period Classification of the Elements which is derived from a Ni/Al/doping element metallurgic precursor alloy and wherein the doping element/Ni ratio by weight is between 0.05 and 10%, is exposed to a nitrile in a liquid reaction medium which dissolves the nitrile along with a hydroxide and thereby hydrogenating said nitrile. The hydroxide in U.S. Pat. No. 5,777,166 is at least one inorganic base selected from the group consisting of LiOH, NaOH, KOH, RbOH, and CsOH. The liquid reaction medium is described to advantageously be an at least partially aqueous reaction medium and according to a preferred characteristic of said process also the amine targeted by the process is incorporated in the reaction medium. The examples disclosed in U.S. Pat. No. 5,777,166 describe the preparation of hexamethylenediamine (HMD) by hydrogenation of adiponitrile in a HMD/ethanol/water mixture. First the catalyst is rinsed with water prior to introduction into a reactor. Then the liquid reaction medium, comprising the diamine and water is added. Then the hydroxide is introduced with the amount of water, necessary for adjusting the required water percentages. The known process is claimed to have improved selectivity for diamine formation, and on the other hand to reduce the impurities as far as possible.

A disadvantage of the known process is that the selectivity for diamine formation, and reduction of impurities is still not optimal, in particular when succinonitrile is the nitrile to be hydrogenated.

The aim of the present invention is to provide a process for the catalytic hydrogenation of a nitrile in the presence of an amine and a liquid-rinsed Raney-type catalyst that is contacted with a hydroxide wherein the selectivity for diamine formation is further improved, and formation of impurities is further reduced, relative to the known process.

This is achieved with the process according to the invention, wherein the freshly prepared and liquid-rinsed Raney-type catalyst is contacted with at least a part of the hydroxide prior to contacting said catalyst with the amine.

The advantage of the inventive process is that it allows formation of a diamine from the hydrogenation of a dinitrile, with a higher selectivity of diamine formation with respect to the starting dinitrile, and a lower amount of impurities, than the process per the prior art. Furthermore, the reaction speed for conversion of the nitrile into the corresponding amine and by-products is increased in respect to the process per the prior art.

In the context of the application the reaction speed of the nitrile is understood to be the ratio between the amount of reaction product or products, comprising the corresponding amine and by-products, formed per second and the instantaneous amount of nitrile present in the reaction medium wherein the hydrogenation process is carried out.

In the context of the application the term freshly prepared catalyst is understood a catalyst that has not been used in the catalytic process before it was rinsed. It may have been stored for shorter or longer time. After said storage it can be rinsed prior to the further use in the process according to the invention.

In the context of the application the term by-product is understood to be any other product than the targeted amine formed by conversion of the nitrile in the hydrogenation process.

In the context of the application the selectivity of the hydrogenation process is understood to relate to the ratio between the targeted amine and other products formed in the hydrogenation process. The selectivity may be expressed as the molar between the respective amounts in which the targeted amine and by-products are formed.

Suitable nitrites that can be used in the process according to the invention are, for example, nitrile substituted aliphatic compounds and nitrile substituted aromatic mononitriles. The aliphatic groups in the aliphatic compounds may be linear or branched. The nitrites may be, for example, mononitriles, i.e. compounds comprising one nitrile group, and dinitriles, i.e. compounds comprising two nitrile groups.

Suitable mononitriles are, for example, nitrites of the formula R—CN, with R being a linear or branched alkyl radical group with 1-20 C-atoms, such as methylnitril (comprising a C1-alkyl radical group), ethylnitril (comprising a C2-alkyldiradical group) butylnitril (comprising a C4-alkylradical group), pentylnitril (comprising a C2-alkyldiradical group) and hexylnitril (comprising a C6-alkylradical group).

Suitable dinitriles are, for example, dintriles of the formula NC—$R^1$—CN, with $R^1$ being a linear or branched alkyl diradical group with 1-20 C-atoms, such as succinonitrile (comprising a C2-alkyldiradical group), and adiponitrile (comprising a C4-alkyldiradical group).

Preferably, the nitrile is a dinitrile. Dinitriles are much more prone to formation of by-products, and hydrogenation of dinitriles is generally accompanied with the formation of cyclisation products and/or higher oligomers. With the process according to the invention, comprising hydrogenation of dinitriles, the increase in selectivity of converting the nitrile groups in amine groups, and thereby forming the targeted diamine, is even larger than for monoamines.

More preferably, the dinitrile is succinonitrile. Generally, succinonitrile is more prone to forming the corresponding cyclisation product, in casu pyrrolidine (PRD), than most (if not all) other dinitriles, with a very low selectivity for diamine formation, in casu diaminobutane. For example, in a hydrogenation process wherein a Raney Ni catalyst is used in absence of hydroxide and amine, the selectivity for diaminobutane (DAB) formation is only about half of that of PRD (see for example F. Devred et al in Applied Catalysis A: General 6454 (2002) 1-1). For the situation, wherein the hydrogenation process is carried out in the presence of a specific cyclic urea compound, it is reported that the DAB conversion expressed as a mole percentage of converted SN is 45-74%, whereas the corresponding PRD conversion is about 25-14% (JP-A-2001-172229). In case of the known process the selectivity for DAB is improved, however, only up to a DAB-conversion level of about 76%, with formation of by-products, including PRD, estimating to a level of about 18%. With the process according to the invention, comprising hydrogenation of SN, the selectivity for the corresponding diamine is even much further improved.

In the process according to the invention, the hydrogenation of the nitrile is carried out in the presence of an amine. Suitable amines that can be used for this purpose are monoamines, diamines and higher amines.

Suitable monoamines are, for example, amines of the formula $R^2—NH_2$, with $R^2$ being an linear or branched alkyl radical group with 1-20 C-atoms, such as methylamine, ethylamine, propylamine, butylamine, isobutyl amine, pentylamine and 2-ethylhexylamine.

Suitable diamines are, for example, diamines of the formula $H_2N—R^3—NH_2$, with $R^3$ being an linear or branched alkyl diradical group with 1-20 C-atoms, such as ethylenediamine, propylenediamine, diaminobutane pentamethylene-diamine and hexamethylenediamine.

Preferably, the amine is a diamine chosen form the group consisting of ethylenediamine, propylenediamine, diaminobutane, pentamethylene-diamine and hexamethylenediamine, having the advantage that these diamines are very suitable precursors for preparing polymers such as polyamides.

More preferably, the amine is the amine whose preparation is targeted by the hydrogenated process.

In a more preferred embodiment the hydrogenation process comprises hydrogenation of succinonitrile and the diamine is diaminobutane.

Raney type catalysts that are suitable as a hydrogenation catalyst, are generally prepared from an aluminium rich aluminium-metal alloy, wherein the metal is a metal such as nickel, cobalt, iron, copper, platinum, palladium and/or ruthenium, and leaching at least partially the aluminium from the alloy by treatment with a strong alkaline solution comprising a hydroxide compound, such as a solution of any of the alkali hydroxides LiOH, NaOH, KOH, RbOH and/or CsOH, a solution of any of the alkali earth hydroxides, such as $Ca(OH)_2$ and/or $Mg(OH)_2$, or a solution of ammonium hydroxide. Preferably, the alkaline solution is a solution of an alkali hydroxide of a mixture of alkali hydroxides). Said solution typically comprises between 5 and 30 weight % of alkali hydroxide. By said leaching, highly porous, high surface area, activated catalysts consisting of agglomerates of crystallites of a metal residue, for example Ni-agglomerates when starting form an Al/Ni alloy and Co-agglomerates when starting from an Al/Co alloy, are formed. The metal alloy may also comprise a doping element, consisting of secondary metal elements. The metal elements that can be used as doping element typically are transition elements, which include Fe, Cr, Mn, V, Mo, Zr, Ta, and Ti. The doping elements, which are conveniently introduced into the melt of the aluminium-metal alloy, modify the structural and electrical factors of the Raney catalyst. Type of aluminium-metal alloy, type and amount of doping element, as well as the conditions of the leaching process (i.e. temperature, alkaline hydroxide concentration, duration of the process) and residual aluminium content in the Raney metal catalyst all constitute variables that have an effect on the activity, selectivity and stability of the catalyst.

Raney type catalysts that are advantageously used in the inventive process, are Raney-Ni and Raney-Co catalysts or combinations thereof More preferably, a Raney-Ni catalyst or a Raney-Co catalyst doped with Fe and/or Cr is used. The advantage of this more preferred embodiment is a higher selectivity for formation of the targeted amine in the hydrogenation of the nitrile in the process according to the invention.

After the leaching process the catalyst is generally thoroughly washed to remove aluminium hydroxide and aluminium crystallites formed during said leaching process. Washing is typically done with water or alkaline solutions in water, though other liquids may be used as well as long as they are effective, and washing is typically done for several times. After the washing step the catalyst is generally stored in a diluted alkaline solution, or in another medium suitable for storing said catalyst. In common practice, the catalyst, before being used in a hydrogenation process, is rinsed with water and than brought into contact with the reaction medium.

In the process according to the invention, the catalyst, after having been stored in an alkaline solution, or other medium suitable for storing said catalyst, is rinsed with a rinsing liquid and next contacted with the hydroxide prior to contacting the catalyst with the amine. The rinsing step is performed to remove most if not all, most preferable all of the alkaline solution or other medium under which the catalyst has been stored.

A suitable rinsing liquid is, for example, water or a water/methanol mixture, preferably water. The advantage of using water as the rinsing liquid is that more reproducible results are obtained in the further use of the catalyst.

Suitable hydroxides that can be used in the process according to the invention are the alkali hydroxides LiOH, NaOH, KOH, RbOH and CsOH. Preferably the hydroxide is KOH, RbOH, CsOH or a mixture thereof. The advantage of a hydroxide chosen from this group is a higher selectivity for amine formation.

More preferably KOH and/or RbOH is chosen as the hydroxide since this gives the highest reaction speed.

Most preferably KOH is used, since this gives the highest reaction speed.

The hydroxide is typically used in an amount between 1 weight % and 20 weight %, relative to the weight of the Raney catalyst. Lower amounts than 1 weight % may be used, but these are less effective. Higher amounts than 20 weight % may be used as well, but this is neither very effective since this does not contribute to a further performance of the catalyst.

Preferably, the hydroxide is used in an amount between 1 weight % and 15 weight %, more preferably between 2 weight % and 12 weight %, most preferably between 4 weight % and 10 weight %, relative to the weight of the Raney catalyst. A higher minimum amount has the advantage that the reaction speed of the nitrile and the selectivity for the amine formation are higher, whereas a lower maximum amount has the advantage that stability of the catalyst is improved thus allowing a lower catalyst regeneration frequency.

With KOH as the hydroxide the optimum amount is around 6 weight % relative to the weight of the Raney catalyst.

In the process according to the freshly prepared Raney type catalyst might have been stored under an alkaline solution prior to being liquid rinsed.

Preferably, the catalyst has been stored under an alkaline solution comprising an alkali hydroxide, which is different from the alkali hydroxide with which the catalyst is contacted after rinsing. This has the advantage that the selectivity of the catalyst is enhanced. More preferably the alkali hydroxide with which the catalyst is contacted after rinsing is chosen from the group consisting of potassium hydroxide, rubidium hydroxide and cesium hydroxide. Most preferably, the freshly prepared Raney type catalyst has been stored under an alkaline solution comprising sodium hydroxide prior to being liquid rinsed, and is contacted with potassium hydroxide prior to contacting the catalyst with the amine.

In the process according to the invention, prior to contacting the catalyst with the amine, the catalyst is contacted with at least part of the hydroxide.

Preferably, this part is at least 10 weight % of the hydroxide, relative to the total weight of hydroxide with which the catalyst is contacted. More preferably, the part is at least 20%, more preferably at least 50%, and most preferably all the hydroxide. The advantage of a larger part of hydroxide with which the catalyst is contacted prior to contacting the catalyst with the amine, is that the reaction speed of the nitrile and the selectivity for the amine formation are higher.

In a preferred mode of the invention, the catalyst, after it is contacted with the at least part of the hydroxide, is kept as is for a somewhat longer time-period, before it is contacted with the amine. Preferably, said time period is at least 15 minutes, more preferably at least 1 hour, even more preferably at least 6 hours, and most preferably at least 24 hours. The advantages of a longer time period according to the preferred mode of the invention are even higher selectivity for the amine formation and/or even higher reaction speed.

The hydrogenation of the succinonitrile in the process according to the invention is preferably carried out in a liquid reaction medium, capable of dissolving the nitrile to be hydrogenated. Said liquid reaction medium comprises at least one liquid component, and optionally at least one other component that is soluble in said at least one liquid component under the conditions of the hydrogenation step in the process. The liquid reaction medium may comprise a liquid amine, water or another solvent, as the at least one liquid component.

Suitable solvents that may be present in the liquid reaction medium are liquid alcohols and liquid amides. Suitable alcohols are, for example, methanol, ethanol, propanol, isopropanol, butanol, glycols, such as ethylene glycol and/or propylene glycol, liquid polyols and/or mixtures of said compounds. Suitable amides are, for example, dimethylformamide and dimethylacetamide.

In an advantageous embodiment, the liquid reaction medium is an at least partially aqueous liquid reaction medium, comprising water next to the amine. Water, if comprised in the liquid reaction medium, is typically present in an amount of at most 50 weight %, advantageously at most 20 weight %, relative to the weight of the total reaction medium. More preferably, the water content of the reaction medium is between 0.1 weight % and 15 weight %, still more preferably between 4 weight % and 10 weight %, relative to the weight of the total reaction medium. The advantage of the amount of water between the narrower boundaries is a higher reaction speed in combination with a higher selectivity.

The process according to the invention can be carried out by first contacting the catalyst with the at least part of the hydroxide, then contacting the catalyst with the amine, optionally prior to, simultaneously with or subsequent to the optional other components making up for the reaction medium, thus forming a reaction mixture of catalyst and reaction medium, and then heating the reaction mixture to, or close to, the selected reaction temperature at which the hydrogenation is to be carried out. The heating step, and preferentially also the preparation step for forming said reaction mixture, are typically carried out under an inert gas atmosphere, for example, under a nitrogen gas atmosphere.

The reaction mixture typically comprises the catalyst in a concentration of between 0.5 weight % and 30 weight %, preferably between 1 weight % and 20 weight %, more preferably between 2 weight % and 15 weight %, the weight % relative to the total weight of the reaction mixture.

The concentration of the amine, preferably the targeted amine, in the reaction medium is advantageously between 50% and 99% by weight with respect to all the liquid components in the said reaction medium, more preferentially, still, is between 60% and 99% by weight, even more preferentially between 70 and 96% by weight. A high minimal amount has the advantage of a higher selectivity for the targeted conversion of nitrile into amine, whereas a lower maximum amount allows a higher water content giving an improved selectivity and/or a higher content of nitrile resulting in a better use of reactor capacity.

The reaction temperature generally is between room temperature (approximately 20° C.) and at most 150° C. Preferably, the reaction temperature is at most 120° C., more preferably at most 100° C. Also preferably the reaction temperature is at least 40° C., more preferably at least 60° C. Very suitably, the temperature is between 70° C. and 90° C. The advantage of a higher minimum reaction temperature is a higher reaction speed. The advantage of a lower maximum reaction temperature is a higher selectivity for conversion of the nitrile in the targeted amine.

Prior to, simultaneously with or subsequent to the heating the reaction mixture, hydrogen gas is introduced into said reaction mixture by applying a hydrogen gas pressure. Appropriately, the hydrogen gas pressure that is applied is between 1-100 MPa. A higher hydrogen gas pressure may be applied. Suitably the hydrogen gas pressure is between 50 and 90 MPa. In case there is still nitrogen gas, or another inert gas, present, the hydrogen gas pressure referred to corresponds with the partial pressure of the hydrogen gas. A higher minimum hydrogen pressure is advantageously applied for attaining a higher reaction speed. A lower maximum hydrogen pressure is that less expensive equipment can be used for carrying out the hydrogenation process.

The nitrile is added into the reaction mixture being under hydrogen gas pressure. The nitrile is typically introduced in an amount of at most 300 g per liter of reaction mixture. Preferably this amount is between 10 and 200 g per liter of reaction mixture, more preferably between 20 and 150 g per liter of reaction mixture and most preferably between 40 and 100 g per liter of reaction mixture. A lower maximum amount has the advantage of a higher selectivity, whereas a higher minimum amount ahs the advantage of a better use of the reactor capacity.

Also preferably, the nitrile is added to the reaction mixture in a weight ratio, relative to the weight of the catalyst, between 0.2:1 and 5:1, more preferably in a weight ratio between 0.5:1 and 2:1.

In a preferred mode of the invention, the process comprises (a) preparing a reaction mixture of the catalyst that has been contacted with the hydroxide, in a liquid reaction medium under an inert gas atmosphere, wherein the reaction mixture comprises 0.5-30 weight % of catalyst relative to the total weight of reaction mixture, and the liquid reaction medium comprises 50-100 weight % amine and 0-50 weight % water, relative to the total weight of the liquid reaction medium, (b) applying a hydrogen pressure between 1 and 100 bar, and (c) adding the nitrile to said reaction mixture in a weight ratio, relative to the weight of the catalyst, between 0.1:1 and 10:1, thereby converting the nitrile in the corresponding amine.

The process according to the invention may suitably be carried out as a batch process as well as a continuous process.

The order given above only corresponds to a preferred, but not limiting form of the process according to the invention. By virtue of all the advantageous arrangements mentioned above, the process according to the invention makes it possible to hydrogenate nitrites to amines in a selective, fast, convenient and economical way. This process is perfectly suitable for converting succinonitrile to diaminobutane, which is the precursor of polyamide-4,6.

The invention will further be illustrated with the following examples without being limited thereto.

Materials

Catalyst A RaNi catalyst doped with Fe and Cr, slurry in water

Catalyst B RaNi catalyst doped with Fe and Cr, slurry in sodium hydroxide solution Ethylendiamine: industrial grade (99% pure)

Succinonitrile: industrial grade (99% pure)

Hydrogen gas: industrial grade (99.99 pure)

Nitrogen gas: industrial grade (99.9 pure)

Equipment.

Experiments were carried out using a 100 ml lab-scale Premex autoclave reactor, made from Hastelloy C metal. The reactor was fitted into a housing, enabling experimentation up to pressures of 220 bar and temperatures up to 250° C. The reactor was equipped with a hydrogen supply inlet connected with a hydrogen gas supply, a stirrer connected to a driving motor (ex Lenz), which could be used up to a stirring speed of 2000 rpm, an injection vessel for adding components into the reactor and via which injection vessel samples could be taken, and a temperature control system consisting of an cooling water mantle and a heating element.

Preparation of the Liquid Rinsed Catalyst

An amount of the catalyst slurry A corresponding with an amount of 7 g catalyst was weighted into a glass beaker and left to allow the catalyst to precipitate. Than the supernatant liquid was decanted as good as possible and the remaining wet sediment, consisting of a concentrated catalyst slurry was poured into the reactor. Then an amount about 50 ml water was added, the water and sediment were stirred. Then the catalyst was allowed to sediment, and the supernatant water was decanted. This operation of adding water, stirring, sedimentation and decanting was repeated four more times. Thus a concentrate of a liquid rinsed catalyst was obtained.

EXAMPLE I

After preparation of the liquid rinsed catalyst according the general procedure described above, the catalyst was contacted with potassium hydroxide by adding a potassium hydroxide solution in water to the liquid rinsed catalyst, in such an amount corresponding with a KOH/catalyst ratio of 0.1. The resulting mixture was stirred well. Then the catalyst was washed to remove the surplus of water, by adding ethylenediamine (EDA). The ethylenediamine and the slurry of hydroxide contacted catalyst in water were mixed by stirring and subsequently the ethylenediamine/water mixture was decanted from the catalyst sediment. Then the reactor content was replenished with fresh ethylenediamine up to a total reactor content of 82 g with fresh solvent, after which the reactor was brought into the autoclave housing, and the system is closed. The reactor was brought to a pressure of approximately 20 MPa by filling the reactor with nitrogen gas and subsequently discharging the gas pressure to expel the air from the reactor, the injection vessel and the pipe sections. This cycle was increasing the nitrogen gas pressure and discharging the gas pressure was repeated two more times. During the third time, the pressure is first increased to 40 MPa and then to 60 MPa, to detect possible leakages in the set-up. Then the first cycle was repeated using hydrogen gas of 20 MPa instead of nitrogen gas. Then the stirring was set at 1800 rpm and the reactor temperature was set to the selected reaction temperature of 80° C. Then the reactor was left for attaining the reaction temperature. During conditioning of the reactor, 7 g of succinonitrile was charged to the injection vessel. Then the injection vessel was brought to a pressure of 70 MPa with hydrogen gas. When the process conditions in the reactor had stabilized for 15 minutes, the valve between the reactor and the injection vessel was opened (which moment was recorded as t=0), and the succinonitrile was shot into the reactor with the help of the overpressure in the injection vessel, thus allowing the hydrogenation reaction of succinonitrile to take place. During the reaction, the hydrogen gas feed to the reactor remained open to supplement the hydrogen gas consumed by the reaction. The conversion of succinonitrile was followed by taking samples from the liquid reactor content at regular time intervals and analyzing the composition of the samples by GC. After completion of the reaction, i.e. after 100% conversion of the succinonitrile, the reactor was cooled down to room temperature, while the stirring speed was reduced to 500 rpm. After the reactor had cooled down to 25° C., the stirrer was stopped and the pressure is released from the reactor. Then the reactor was freed from the housing and the liquid reactor content was decanted from the catalyst sediment. The liquid reactor content was analyzed with regard to $H_2O$, acrylobutyronitril (ABN), diaminobutane (DAB) and pyrollidone (PRD) content. The analytical results are presented in Table I.

EXAMPLE II

Example I was repeated except that the catalyst was contacted with a potassium hydroxide solution in an amount corresponding with a KOH/catalyst ratio of 0.04 instead of 0.1. The analytical results are presented in Table I.

EXAMPLE III

Example I was repeated except that after the catalyst was contacted with the potassium hydroxide solution 4 days was waited before the catalyst was washed with ethylene diamine to remove the surplus of water. The analytical results are presented in Table I.

EXAMPLE IV

Example I was repeated except that the catalyst was contacted with a first amount of potassium hydroxide solution corresponding with a KOH/catalyst ratio of 0.05; subsequently the catalyst was washed with ethylene diamine, decanted and replenished with ethylenediamine as in Example I and then a second amount of potassium hydroxide solution corresponding with a KOH/catalyst ratio of 0.05 was added. The analytical results are presented in Table I.

Comparative Experiment A

Experiment I was repeated except that the potassium hydroxide solution corresponding with a KOH/catalyst ratio of 0.1 was added after the catalyst was washed with ethylene diamine, decanted and replenished with ethylenediamine. The analytical results are presented in Table I.

TABLE I

Results of Examples I-IV and Comparative Experiment A.

| Experiment | Example I | Example II | Example III | Example IV | Comparative Experiment A |
|---|---|---|---|---|---|
| KOH/RaNi | 0.1 | 0.04 | 0.1 | 0.1 | 0.1 |
| Moment of hydroxide contact with respect to EDA contact | before | before | before | 50% before 50% after | after |
| Time-period between hydroxide contact and EDA contact | Few minutes | Few minutes | 4 days | First amount few minutes | |
| ABN (mole %) [a] | 0.5 | 0.5 | 0 | 2 | 12 |
| DAB (mole %) [a] | 95 | 94 | 96 | 90 | 76 |
| PRD (mole %) [a] | 3 | 4 | 3 | 5 | 6 |
| H2O gehalte (weight %) [b] | 5.8 | 6.0 | 7.3 | 7.2 | 5.9 |

[a] relative to the original molar amount of succinonitrile
[b] relative to the total reactor content

EXAMPLE V

Example I was repeated except that the catalyst was contacted with a cesium hydroxide solution in an amount corresponding with a cesium hydroxide/catalyst ratio of 0.1. The analytical results are presented in Table II.

EXAMPLE VI

Example I was repeated except that the catalyst was contacted with a rubidium hydroxide solution in an amount corresponding with a rubidium hydroxide/catalyst ratio of 0.1. The analytical results are presented in Table II.

EXAMPLE VII

Example I was repeated using the same amount of potassium hydroxide. The analytical results are presented in Table II.

EXAMPLE VIII

Example I was repeated except that the catalyst was contacted with a sodium hydroxide solution in an amount corresponding with a sodium hydroxide/catalyst ratio of 0.1. The analytical results are presented in Table II.

EXAMPLE IX

Example I was repeated except that the catalyst was contacted with a lithium hydroxide solution in an amount corresponding with a lithium hydroxide/catalyst ratio of 0.1. The analytical results are presented in Table II.

TABLE II

Results of Examples V-IX.

| Experiment | Example V | Example VI | Example VII | Example VII | Example IX |
|---|---|---|---|---|---|
| Alkalihydroxide | CsOH | RbOH | KOH | NaOH | LiOH |
| alkalhydroxide/RaNi ratio | 0.1 | 0.1 | 0.1 | 0.1 | 0.1 |
| ABN (mole %) [a] | 5 | 1 | 1 | 5 | 11 |
| DAB (mole %) [a] | 90 | 92 | 94 | 85 | 67 |
| PRD (mole %) [a] | 3 | 3 | 3 | 4 | 14 |
| H2O gehalte (weight %) [b] | 7.3 | 5.8 | 6.0 | 7.2 | 9.2 |

[a] relative to the original molar amount of succinonitrile
[b] relative to the total reactor content

EXAMPLES X

Example I was repeated except that instead of catalyst A, catalyst B, i.e. the catalyst stored under sodium hydroxide solution was used. The selectivity of the reaction for diamine formation was improved showing a DAB/PRD ratio of 47.

The invention claimed is:

1. Process for the catalytic hydrogenation of a nitrile in the presence of an amine, a hydroxide and a freshly prepared and liquid-rinsed Raney-type catalyst, characterized in that the catalyst is contacted with at least a part of the hydroxide prior to contacting the catalyst with the amine.

2. Process according to claim 1, wherein the nitrile is a dinitrile.

3. Process according to claim 1, wherein the amine is a diamine.

4. Process according to claim 1, wherein the catalyst is a Ra—Ni-type catalyst or a Ra—Co-type catalyst.

5. Process according to claim 1, wherein the hydroxide is chosen from the group consisting of potassium hydroxide, rubidium hydroxide and cesium hydroxide.

6. Process according to claim 1, wherein the hydroxide is used in an amount of between 1 weight % and 15 weight %, relative to the weight of the catalyst.

7. Process according to claim 1, wherein the part of the hydroxide, with which the catalyst is contacted prior to contacting the catalyst with the amine, is at least 10 weight %, relative to the total weight of hydroxide, with which the catalyst is contacted.

8. Process according to claim 1, wherein prior to rinsing the catalyst is stored under an alkaline solution comprising an alkali hydroxide, which is different from the alkali hydroxide with which the catalyst is contacted after rinsing.

9. Process according to claim 1, wherein the catalyst, after it has been contacted with at least part of the hydroxide, is kept as is for a period of at least 15 minutes prior to contacting the catalyst with the amine.

10. Process according to claim 1, wherein the hydrogenation is carried out in an at least partially aqueous liquid reaction medium.

11. Process according to claim 1, comprising
  (a) preparing a reaction mixture of the catalyst contacted with the hydroxide in a liquid reaction medium under an inert gas atmosphere, wherein the reaction mixture comprises 0.5-30 weight % of catalyst relative to the total weight of reaction mixture, and the liquid reaction medium comprises 50-100 weight % amine and 0-50 weight % water, relative to the total weight of the liquid reaction medium, (b) applying a hydrogen pressure between 1 and 100 bar, and (c) adding the nitrile to said reaction mixture in a weight ratio, relative to the weight of the catalyst, between 0.1:1 and 10:1, thereby converting the nitrile in the corresponding amine.

* * * * *